United States Patent [19]

Arcan et al.

[11] 4,066,082
[45] Jan. 3, 1978

[54] FORCE APPLICATOR INCLUDING INDICATOR

[75] Inventors: Mircea Arcan, Ramat Hasharon; Gordon Robin; Ariel Simkin, both of Jerusalem, all of Israel

[73] Assignee: Ramot University Authority for Applied Research and Industrial Development Ltd., Tel Aviv, Israel

[21] Appl. No.: 678,609

[22] Filed: Apr. 20, 1976

[30] Foreign Application Priority Data

Apr. 24, 1975 Israel ......................................... 47164

[51] Int. Cl.² .......................... A61B 17/00; G01B 5/30; G01B 11/18
[52] U.S. Cl. ................................ 128/303 R; 73/88 A; 356/33
[58] Field of Search ............ 128/69, 78, 92 EA, 92 R, 128/303 R; 356/32, 33, 34, 35

[56] References Cited

U.S. PATENT DOCUMENTS

| 3,034,344 | 5/1962 | Zandman et al. | 73/88 A X |
| 3,477,284 | 11/1969 | Schwallie et al. | 356/33 X |
| 3,651,584 | 3/1972 | Perry | 356/33 X |
| 3,785,381 | 1/1974 | Lower et al. | 128/361 X |

FOREIGN PATENT DOCUMENTS

| 303,821 | 2/1955 | Switzerland | 128/321 |
| 205,222 | 11/1967 | U.S.S.R. | 128/321 |

Primary Examiner—Channing L. Pace
Attorney, Agent, or Firm—Benjamin J. Barish

[57] ABSTRACT

A device for indicating the force applied by a tool comprises a bar arranged so as to be deflected in accordance with the force applied, a pair of spaced stops carried by the bar, a frame enclosing both stops with one end of the frame engaging one side of one stop and the opposite end of the frame extending past the other stop to define a space therebetween, and a load sensing member disposed in the latter space, whereby the deflection of the bar is converted by the two stops and the frame to a compressive force on the load-sensing member. The described load-sensing member is a photoelastic member and the described device in which it is used is a surgical spreader hand tool wherein the photoelastic member indicates to the surgeon the force applied.

6 Claims, 5 Drawing Figures

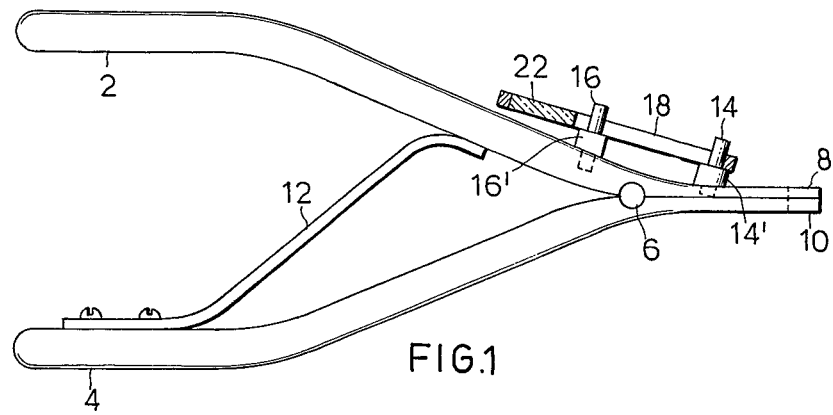
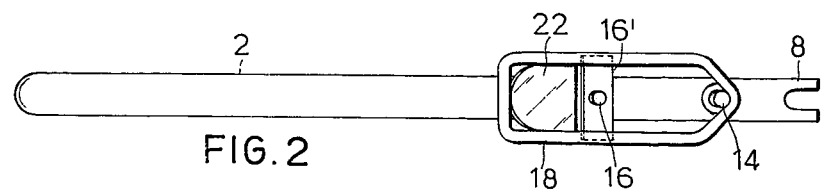
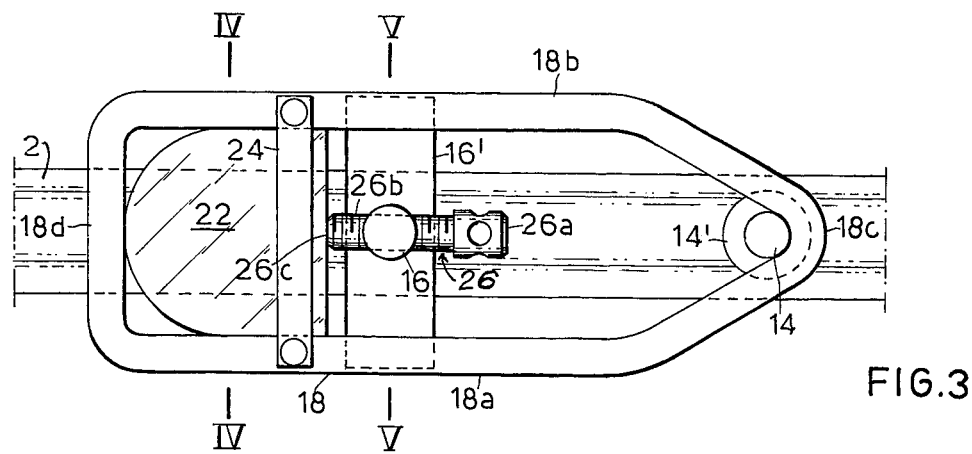
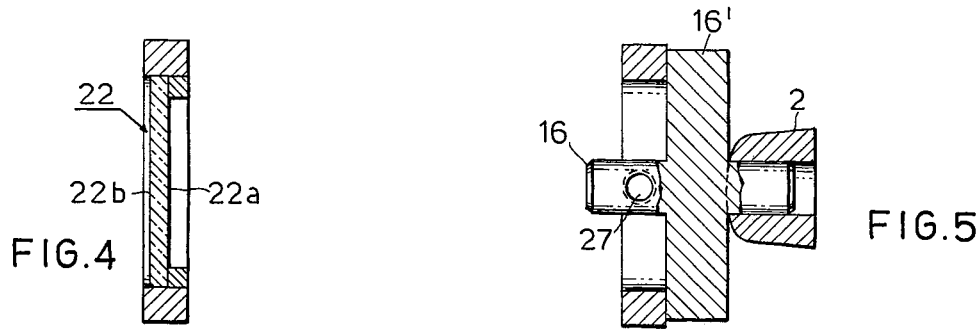

FORCE APPLICATOR INCLUDING INDICATOR

BACKGROUND OF THE INVENTION

The present invention relates to force applicator devices including indicators for indicating the force applied. The invention is particularly useful with respect to surgical tool spreaders for applying an extension force to a part of the human body and for providing an indication of the force applied. The invention is therefore described below with respect to this application, but it will be appreciated that the invention, or various features thereof, could advantageously be used in other applications as well.

Many surgical procedures and other medical treatments, especially in orthopedics, involve the use of force. For instance, scoliosis, which is a lateral curvature of the spine, is corrected through external bracing (Milwaukee brace) or surgically (Harrington rod procedure). In the first one, a longitudinal force is applied between the head and the pelvis together with lateral pressure. In the latter, used for more severe cases, extension forces are exerted directly on the spine. In both cases, the magnitude of the applied force is of vital importance to the success of the treatment. Insufficient force will not produce the desired effect, while excessive force may cause accidents such as fracture of the posterior elements of the vertebrae or paraplegia, which appears to be a consequence of a vascular lesion.

The Harrington rod procedure, today the more common of the two above surgical techniques, uses two hooks and a rod with a series of circumferential grooves. One hook rests against a shoulder at one end of the rod, while the other may slide along the rod. The two hooks are inserted into the posterior elements of the spine at the two ends of the curve. A spreader is used to move one hook along the rod and distract the spine.

During this operation, a considerable force may be applied to the spine. In order to avoid any damage, it has been recommended to have a safety limit of 30 to 40 Kg axial force. Two devices have previously been proposed for indicating the force. One includes a mechanical indicator provided by cutting one handle of the instrument and connecting it back through a leaf spring, using the deflection of the spring as a measure of the force; however, the flexibility of the spring increases the flexibility of the handle, which is not always desired by the surgeon. The other device includes resistance strain gages attached to the spreader as an electrical force transducer; this method, however, involves an expensive measuring system and inconvenient wiring, and moreover, makes direct reading of the force by the surgeon very difficult because the force indication is at some distance from the operation site.

SUMMARY OF THE INVENTION

An object of the present invention is to provide a novel force-applying tool and force-indicator having advantages in the above respects. More particularly, an object of the invention is to provide a force-applying hand tool including a force-indicator which hand tool is of simple, inexpensive and sterilizable, construction, and provides an easily-viewable indication during use of the force applied, making the hand tool particularly useful as a surgical spreader.

According to a broad aspect of the invention, there is provided a device for indicating the force applied by a tool to an object, comprising: a bar constituting a part of said tool so as to be deflected in accordance with the force applied thereby to the object; a pair of spaced stops carried by the bar; a frame enclosing both stops with one end of the frame engaging one side of one stop and the opposite end of the frame extending past the other stop to define a space between said other stop and said opposite end of the frame; and a load-sensing member disposed in said latter space, whereby the deflection of the bar is converted by the two stops and the frame to a compressive force on the load-sensing member.

According to a further feature, the load-sensing member is a photoelastic member changing its optical properties when subjected to stress to thereby provide an optical indication of the magnitude of the force applied by the device.

According to a further feature, the device is a surgical spreader in which the jaws are designed to apply extension forces to the spine for the surgical correction of scoliosis, the photoelastic member being disposed adjacent to the jaws to facilitate the surgeon's viewing the photoelastic member at the time he views the area worked by the jaws when using the device.

BRIEF DESCRIPTION OF THE DRAWINGS

The invention is herein described, by way of example only, with reference to a preferred embodiment illustrated in the accompanying drawings, wherein:

FIG. 1 is a side elevational view of a surgical spreader such as used in the above-described Harrington rod procedure for treating scoliosis, the spreader including a force-indicator in accordance with the present invention.

FIG. 2 is a top plan view of the spreader of FIG. 1;

FIG. 3 is a fragmentary view corresponding to that of FIG. 2, but enlarged to illustrate the main elements of the indicator;

FIG. 4 is a sectional view along lines IV—IV of FIG. 3; and

FIG. 5 is a sectional view along lines V—V of FIG. 3.

DESCRIPTION OF THE PREFERRED EMBODIMENT

The surgical spreader illustrated in the drawings is a hand tool comprising of pair of pivotable bars 2, 4, pivotable about pivot 6, and carrying a pair of jaws 8, 10 for applying an extension force to distract the spine during the above-described Harrington procedure for treating scoliosis. A leaf spring 12, fixed to handle 4 and bearing against handle 2, normally maintains the spreader in its closed condition as illustrated in FIG. 1.

According to the invention, a pair of pins 14, 16 are fixed to handle bar 2, the pins being spaced from each other along the longitudinal axis of the handle bar. In the illustrated arrangement, pin 14 is fixed on one side of pivot 6 and the second pin 16 is fixed on the other side of the pivot. Both pins are preferably of steel and each may be fixed by boring a hole in the handle bar and press-fitting the pin therein.

The bottom of pin 14 is formed with an enlarged cylindrical base 14′, and the bottom of pin 16 is formed with a rectangular base 16′, both as shown in FIGS. 1 and 3. A steel frame 18 is supported by the enlarged bases 14′, 16′ of the two pins. Frame 18 is generally rectangular in profile, including two parallel walls 18a, 18b, but the front wall 18c is V-shaped while its back wall 18d is substantially straight. The front wall 18c of frame 18 engages one side of pin 14, whereas the rear wall 18d extends past the other pin 16, defining a space for receiving a photoelastic member or unit 22.

Photoelastic unit 22 is of a known construction, including a photoelastic element 22a (FIG. 4) which is reflectively coated and has a circular polarizer 22b on the top thereof. When the photoelastic unit is subjected to stresses, it changes its optical properties, namely causing isochromatics to develop, the number, color and location of which provide an indication of the force applied. The elements of the photoelastic unit 22 may be conveniently retained in place by a cross-bar 24 overlying the unit and secured at its opposite ends to frame 18. If desired, the unit may be covered by a transparent plastic window (not shown).

A threaded element 26 is threaded within a bore 27 (FIG. 5) in pin 16. Element 26 includes a head 26c bearing against the photoelastic unit 22, a threaded shank 26b threaded within bore 27 in pin 16, and a tail 26a formed with openings or recesses to receive a tool for rotating element 26 and thereby advancing its head 26c towards or away from the photoelastic unit 22.

It will be seen that pin 14 on handle bar 2 of the spreader constitutes one stop, and head 26c of element 26 threaded through bore 27 in pin 16 constitutes a second stop spaced longitudinally of the handle bar. As the handle bar is deflected by the stress due to the force applied by jaws 8, 10, steel frame 18 converts the deflection of the handle bar to a compressive force applied to the photoelastic unit 22 by means of rear wall 18d of the frame, which is displaced with fixed pin 14, and head 26c of element 26 which is displaced with pin 16. The above-described optical change resulting from the compressive force applied to the photoelastic unit 22 provides an optical indication of the magnitude of the force applied.

Thus, the spreader illustrated provides an easily viewable indication of the force applied during the actual use of the spreader. In addition, the provision of threaded element 26, which may be adjusted within bore 27 formed in fixed pin 16, provides a simple arrangement for compensating for temperature variations and also for zero adjustment. Before the tool is to be used, the user merely adjusts threaded element 26 until its head 26c presses lightly against the photoelastic unit 22, this being easily viewable by the optical change in the photoelastic unit.

If desired, the photoelastic unit 22 may include a scale along its axis to provide for calibration directly into units of force. However, it was found that the user quickly learns to correlate the force he applies to the indication he views from the photoelastic unit, at least with sufficient accuracy for use in the above-displayed surgical technique. Great accuracy is not required in this technique, it being sufficient that the user is apprised of the approximate magnitude of the force being applied so as to make sure he is within the safe limits.

What is claimed is:

1. A device for indicating the force applied by a tool to an object, comprising: a bar constituting a part of said tool so as to be deflected in accordance with the force applied thereby to the object; a pair of spaced stops carried by the bar; a frame enclosing both stops with one end of the frame engaging one side of one stop and the opposite end of the frame extending past the other stop to define a space between said other stop and said opposite end of the frame; and a load-sensing member disposed in said latter space, whereby the deflection of said bar is converted by the two stops and the frame to a compressive force on the load-sensing member.

2. A device according to claim 1, wherein one stop is a first pin fixed at one point on the bar, and the other stop is an adjustable element carried by a second pin fixed at a second point on the bar, said adjustable element being presettable with respect to the load-sensing member to provide for zero adjustment and to enable compensation for temperature variations.

3. A device according to claim 2, wherein said adjustable element includes a head engageable with the load-sensing member, and a threaded shank threaded in a transverse bore formed in the second pin.

4. A device according to claim 1, wherein said load-sensing member is a photoelastic member changing its optical properties when subjected to stress to thereby provide an optical indication of the magnitude of the force applied by the device.

5. A device according to claim 4, in combination with a hand tool including a pair of pivotable handle bars graspable by the user and having a pair of jaws for applying the force, one of said pivotable handle bars constituting said bar deflected in accordance with the force applied by the tool.

6. A device according to claim 5, wherein the tool is a surgical spreader in which the jaws are designed to apply extension forces on the spine for the surgical correction of scoliosis, the photoelastic member being disposed adjacent to the jaws to facilitate the surgeon's viewing the photoelastic member at the time he views the area worked by the jaws when using the device.

* * * * *